US006348503B1

(12) United States Patent
Squires

(10) Patent No.: US 6,348,503 B1
(45) Date of Patent: *Feb. 19, 2002

(54) METHOD AND TOPICAL TREATMENT COMPOSITION FOR HERPESVIRUS HOMINIS

(75) Inventor: Meryl Squires, Elmhurst, IL (US)

(73) Assignee: Meryl J. Squires, Barrington Hills, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/600,217

(22) Filed: Feb. 12, 1996

(51) Int. Cl.$^7$ .............................................. A61K 31/14
(52) U.S. Cl. ....................................... 514/642; 514/643
(58) Field of Search .................................. 514/642, 643

(56) References Cited

U.S. PATENT DOCUMENTS

| | | | | | |
|---|---|---|---|---|---|
| 4,283,421 A | * | 8/1981 | Ray | ............................. | 424/317 |
| 4,585,656 A | * | 4/1986 | Rosenthal et al. | ........ | 424/195.1 |
| 4,661,354 A | * | 4/1987 | Finnerty | ...................... | 424/642 |
| 4,760,079 A | * | 7/1988 | Baldone | ...................... | 514/642 |
| 4,797,420 A | * | 1/1989 | Bryant | ........................ | 514/643 |
| 4,855,284 A | * | 8/1989 | Emoedi | .......................... | 514/8 |
| 4,935,448 A | * | 6/1990 | Baldone | ...................... | 514/642 |
| 5,149,529 A | * | 9/1992 | Ho et al. | ..................... | 514/642 |
| 5,455,033 A | * | 10/1995 | Silverman et al. | ........... | 424/195 |
| 5,461,029 A | | 10/1995 | Backer et al. | .................. | 514/2 |
| 5,554,596 A | | 9/1996 | Mach et al. | ................... | 514/22 |

FOREIGN PATENT DOCUMENTS

WO    WO 96/24367    8/1996

OTHER PUBLICATIONS

Tyler, V. E., "The Honest Herbal, A sensible Guide to the Use of Herbs and Related Remedies", 3rd Edition, pp. 115–117, 1993.*
Tyler, V. E., "The Honest Herbal, The Therapeutic Use of Phytomedicinals", pp. 181–186, 1994.*
Abstract to Wacker et al., "Virus Inhibition by Echinacea Purpurea", Planta Med., 33(1), 89–102, 1978.*
Abstract to Bourbon et al., "Animicrobial formulaitons containing benzalkonium fluorides as active agents", from EP 308,564 A1, Mar. 29, 1989.*
Tyler, V. E., "The Honest Herbal, A sensible Guide to the Use of Herbs and Related Remedies", 3rd Edition, pp. 115–117, 1993.*
Tyler, V. E., "The Honest Herbal, The Therapeutic Use of Phytomedicinals", pp. 181–186, 1994.*
Abstract to "Effect of benzalkonium chloride on HIV and related infections and on other infectious agents", Wainberg et al., Arch. AIDS Res. 1(1), 1987.*
Abstract to "Treatment of herpes infections", Hempel, B., DE 3521143, Dec. 18, 1986.*

* cited by examiner

*Primary Examiner*—Dwayne C. Jones
(74) *Attorney, Agent, or Firm*—Welsh & Katz, Ltd.; Thomas W. Tolpin

(57) ABSTRACT

Improved topical treatment of active phase lesions resulting from recurrent viral infection by herpes simplex virus which includes the use of two primary agents, namely, an aqueous solution of benzalkonium halide, preferably benzalkonium chloride, and a dry form of the herb *Echinacea purpurea*, preferably in powder form. Active phase herpes lesions are wetted with the benzalkonium chloride solution and dusted with the powder form of *Echinacea purpurea* to create a coating on the wetted lesion surface. The coating is maintained on the lesion throughout treatment, and unexpected rapid resolution of the lesions results.

5 Claims, No Drawings

METHOD AND TOPICAL TREATMENT COMPOSITION FOR HERPESVIRUS HOMINIS

DESCRIPTION

1. Technical Field

The present invention generally relates to methods and compositions for the treatment of herpes simplex virus and, in particular, to a method and composition for topical treatment of active phase lesions resulting from recurrent viral infection caused by herpes simplex virus.

2. Background of the Invention

Recurrent viral infection by herpes simplex virus, also known as Herpesvirus Hominis, is characterized by lesions which may appear anywhere on the skin or mucosa. Eventually, the lesion base inflames and develops clusters of small fluid-filled vesicles. Without treatment, the vesicles and lesions will resolve in several days to dry scabs. There are two known strains of herpes simplex virus (HSV), namely, HSV-1, commonly causing herpes labialis and keratitis, and HSV-2, which is usually genital herpes.

Treatment of herpes lesions often includes application of topical agents such as idoxuridine, trifluorothymidine, or acyclovir. In addition, prior art patents also disclose various compositions and methods for topical treatment of symptoms of herpes simplex virus which may include use of anti-viral agents, such as benzalkonium chloride, e.g., U.S. Pat. Nos. 4,283,421, 4,585,656, 4,661,354, 4,760,079, 4,803,224 and 4,797,420. None of these compositions, however, employ the combination of treatment agents disclosed herein.

SUMMARY OF THE INVENTION

According to the present invention, a method and composition has been developed for improved topical treatment of active phase lesions resulting from recurrent infection by herpes simplex virus. The present invention includes the use of two primary agents, namely, an aqueous solution of a benzalkonium halide, preferably benzalkonium chloride, and a dry form of the herb *Echinacea purpurea*, preferably in powder form. In practicing the method of the present invention, an active phase herpes lesion is first thoroughly wetted by spraying or dabbing the benzalkonium chloride solution onto the surface of the lesion. Next, the wetted surface of the lesion is dusted with the powder form of *Echinacea purpurea* to create a coating. The coating must be maintained throughout treatment until the lesion is resolved. Hence, it is preferred that periodically the coating of *Echinacea purpurea* powder be replenished through additional dusting of the lesion surface.

As an alternative to the above method, the present invention also discloses the saturation of a powder form of *Echinacea purpurea* with benzalkonium chloride to create a paste. The paste is applied to cover the lesion surface and, thereby, form a coating. Again, the coating must be maintained during treatment. Frequent replenishment of the coating by reapplication of the paste may, however, be required. The coating is maintained until the active phase of the lesion is resolved.

The present invention can also be practiced by using other alternative methods. For example, the benzalkonium halide and *Echinacea purpurea* composition can be formulated as a liquid, powder, gel, ointment, or any form of such composition as appropriate for topical application. Regardless of the form of the topical composition, the present invention is applied and reapplied to maintain a coating on the afflicted surface.

Preliminary clinical testing on human subjects for both HSV-1 and HSV-2 strains of herpes simplex virus reveals an unexpected and surprising rapid resolution of the active phase lesions, often within twenty-four hours of treatment initiation. In addition, after treatment, there appeared to be longer latency periods between recurrence of the active phases than had been observed prior to topical treatment with the present invention.

Other advantages and aspects of the invention will become apparent upon making reference to the specification and claims.

DETAILED DESCRIPTION OF THE PREFERRED EMBODIMENT

While this invention is susceptible of embodiment in many different forms, there will herein be described in detail a preferred embodiment of the invention with the understanding that the present disclosure is to be considered as an exemplification of the principles of the invention and is not intended to limit the broad aspect of the invention to the illustrated embodiment.

The present invention discloses the use of benzalkonium halide, such as benzalkonium bromide, but preferably benzalkonium chloride, as an anti-viral wetting agent which is used in combination with a dried form of a herbaceous plant from the genus Echinacea and, in particular, *Echinacea purpurea*.

As used in the present invention, benzalkonium chloride is an aqueous solution formed by a 1 part mixture of n-alkyl dimethyl benzyl ammonium chlorides and 750 parts water, preferably sterile water. Benzalkonium chloride in this form is commercially available under the trademark ZEPHIRAN®, and has been known as an anti-infective and anti-viral agent with a moderately long duration period of therapeutic action.

*Echinacea purpurea* is a species of a herbaceous plant of the genera Echinacea, which is one of three genera of the family Asteraceae. *Echinacea purpurea* has a long reported use for its therapeutic and medicinal effects and is commercially available in dry powder form. Some of these reported uses include topical treatment of snake bites, infected wounds, and intra-oral treatment of a sore throat.

In one form of the present invention, benzalkonium chloride is used to wet the surface of an active phase lesion of herpes simplex virus. Then, *Echinacea purpurea*, in dry powder form, is dusted onto the wetted surface of the lesion until a coating is formed on the lesion surface. For the duration of topical treatment, usually about twenty-four hours, the *Echinacea purpurea* coating must be maintained. Therefore, periodic replenishment of the coating by additional dusting of the lesion surface is often required.

In another embodiment of the composition of the present invention, *Echinacea purpurea* powder is wetted until saturated with benzalkonium chloride to form a paste. The wetted paste form of *Echinacea purpurea* powder is then applied and adheres to the surface of the lesion. Again, frequent replenishment of the paste in order to maintain a coating on the surface of the lesion is required for the duration of topical treatment.

In other embodiments of the composition of the present invention, the dry form of *Echinacea purpurea* can be combined with the benzalkonium halide into various forms that can be applied topically. For example, the *Echinacea purpurea* can be combined with the benzalkonium halide to form a liquid, powder, gel, ointment or any form of such composition as appropriate for topical application. These forms of the present invention are also applied to an area having the active phase of herpes simplex virus to coat the area. The treated area is periodically retreated with the topical composition throughout duration of the treatment to maintain the coating. In the liquid, powder, gel and ointment forms, an additional suitable carrier may be added to the composition. For example, a carrier may be added to maintain the composition in a gel form. In the powder form, the benzalkonium halide is used in its dry form and not mixed with water to form a solution.

Surprisingly, the components of this mixture cooperate to give a therapeutic effect and enhanced antiviral activity not suggested by the known properties of benzalkonium chloride and *Echinacea purpurea*. No clear explanation of this unexpected cooperative action has been discovered, although it is postulated that the combination releases an enzyme from Echinacea or produces another by-product which alters or causes a degeneration of the protein coating which encapsulates the viral DNA or renders RNA ineffective.

The present invention has been found particularly effective in the topical treatment of HSV-1 and HSV-2 strains of herpes simplex virus. The following example is given to aid in understanding the invention, and it is to be understood that the invention is not limited to the particular procedures, proportions or materials of the example.

EXAMPLE

Seven human subjects were tested for any beneficial effects from the composition of the present invention. There were a total of twelve active phase lesions which were topically treated according to the present invention. Out of the twelve lesions, nine were genital herpes eruptions and three were cold sore eruptions around the mouth.

Each subject used for this research was diagnosed as having either genital herpes or, in the case of cold sores, presented with very obvious classical symptoms. It was ascertained through obtaining a history from each subject that the disease was well established, and that each subject could identify onset and course of their disease as well as any changes which may occur.

To obtain objective data, the subjects were not told of any action the present invention may have. Two subjects, when being tested during a subsequent active phase, were told that the composition they were using the second time was different when, in actuality, it was the same.

Each time the composition was applied, each subject would experience a tingling sensation for a few seconds. It was observed that there appeared to be some degree of adherence of the compound to any vesicles, if present.

Application of the compound commenced at the first sign of erythematous tissue with the accompaniment of the typical itching, swelling and tingling that indicated onset of the active phase of the disease. In five cases, vesicular eruption had already occurred before the compound could be applied. In these five instances, the compound was applied directly to the vesicles.

A two-step procedure was used. First, the affected area was sprayed or dabbed with the benzalkonium chloride aqueous solution mixture to wet the area. Then the wetted area was dusted or covered with a fine powder of the *Echinacea purpurea* in dried herb form. The compound was reapplied as necessary to maintain coating of the lesion.

Three animal subjects were also used to test for possible dermatologic allergic reactions. In these animal tests, the method used was the same two-step method described above. The compound was applied to the inside of the outer ear of each animal. In all instances, the area being treated was kept coated with the compound for twenty-four hours or until the active phase was resolved.

The animal subjects were observed in one, five, ten and twenty-four hour intervals. The human subjects were either observed or questioned as to their results.

RESULTS

In treatment of all twelve lesions, the results were consistent. Each subject reported that after a relatively short time period, between twenty minutes to an hour, the pain from the lesions subsided. Itching gradually diminished and within twenty-four hours the active phase had ceased, leaving small dry scabs where the vesicles had been or, if application had been administered before vesicles had formed, vesicles never formed.

In each instance, it was reported that the usual symptoms never developed beyond the initial symptoms. The symptoms of fatigue, malaise, weeping sores, painful urination and inguinal glandular swelling did not occur.

One human subject applied the compound to a beginning genital lesion, and failed to reapply the composition after showering and for a period of approximately thirty hours thereafter. Consequently, several vesicles erupted and began to coalesce. The subject proceeded to reapply the composition and, within twenty-four hours, the vesicular outbreak had resolved in the same manner as described with the other human subjects.

After topical treatment with the present invention, it appeared that there were longer latency periods between active phases than previously reported. For example, one subject experienced an outbreak of herpes almost monthly. After using treatment with the present invention, there were lapses in outbreaks of four months, which occurred twice.

The allergy testing performed on the three animal models showed no signs of any dermatologic reactions or allergies.

While the invention has been described with reference to a preferred embodiment, it will be understood by those skilled in the art that various changes may be made and equivalents may be substituted for elements thereof without departing from the broader aspects of the invention. Also, it is intended that broad claims not specifying details of a particular embodiment disclosed herein as the best mode contemplated for carrying out the invention should not be limited to such details.

What I claim is:

1. A method for topical treatment of active phase lesions resulting from herpes, comprising the steps of:

conditioning and treating an active phase herpes lesion on skin or mucosa of a human by sequentially moistening and powdering said active phase herpes lesion;

said moistening comprising wetting an active phase herpes lesion on skin or mucosa of a human with an aqueous solution of benzalkonium chloride and water, said active phase herpes lesion being associated with herpes selected from the group consisting of HSV1, herpes labialis, keratitis, HSV2, and genital herpes;

said powdering the active phase herpes lesion comprising dusting and coating the wetted active phase herpes lesion with powdered Echinacea to form a coating of powdered Echinacea, benzalkonium chloride, and water on the wetted active phase herpes lesion in the absence of aedurid, sodium hydroxide (Na OH), tea tree oil, lapacho extract, and licorice root extract;

said powdered Echinacea consisting only of powdered *Echinacea purpurea*;

said coating on the wetted active phase herpes lesion of HSV1, herpes labialis, keratitis, HSV2, or genital herpes consisting only of powdered *Echinacea purpurea*, benzalkonium chloride, and water; and resolving the active phase herpes lesion by maintaining the coating consisting of powdered *Echinacea purpurea*, benzalkonium chloride and water in the absence of aedurid, sodium hydroxide (Na OH), tea tree oil, lapacho extract, and licorice root extract on the wetted active phase herpes lesion of HSV1, herpes labialis, keratitis, HSV2, or genital herpes until the active phase herpes lesion of HSV1, herpes labialis, keratitis, HSV2, or genital herpes is resolved.

2. A method for topical treatment of active phase lesions resulting from herpes, comprising the steps of:

coating and treating an active phase herpes lesion;

said coating comprising substantially covering said active phase herpes lesion with *Echinacea purpurea* and benzalkonium chloride in the absence of *Echinacea angustofolia*, aliphalic alcohol, aedurid, sodium hydroxide (Na OH), tea tree oil, lapacho extract, and licorice root extract;

said active phase herpes lesion resulting from herpes selected from the group consisting of HSV1, herpes labialis, keratitus, HSV2, and genital herpes; and thereafter resolving the acive phase herpes lesion by maintaining the coating of *Echinacea purpurea* and benzalkonium chloride on the active phase herpes lesion in the absence of *Echinacea angustofolia*, aliphalic alcohol, aedurid, sodium hydroxide (Na OH), tea tree oil, lapacho extract, and licorice root extract until the active phase herpes lesion is resolved.

3. A composition for topical treatment of active phase lesions resulting from herpes, consisting of:

a coating of *Echinacea purpurea* and benzalkonium chloride;

said *Echinacea purpurea* and said benzalkonium chloride being present and cooperating with each other in said coating in the absence of *Echinacea angustofolia*, aliphalic alcohol, aedurid, sodium hydroxide (Na OH), tea tree oil, lapacho extract, and licorice root extract; and said herpes being selected from the group consisting of HSV1, herpes labialis, keratitus, HSV2, and genital herpes.

4. A composition for topical treatment of active phase lesions resulting from herpes, consisting of:

an anti-herpes coating of powdered *Echinacea purpurea* and benzalkonium chloride for substantially covering an active phase herpes lesion in the absence of *Echinacea angustofolia*, aliphalic alcohol, aedurid, sodium hydroxide (Na OH), tea tree oil, lapacho extract, and licorice root extract;

said active phase herpes lesion resulting from herpes selected from the group consisting of HSV1, herpes labialis, keratitus, HSV2, and genital herpes; and said anti-herpes coating being selected from the group consisting of a powder, gel, ointment, and paste.

5. A composition:

a herbaceous botanical of *Echinacea purpurea*, and aqueous benzalkonium chloride, and said herbaceous botanical of *Echinacea purpurea* and said aqueous benzalkonium chloride cooperating with each other to provide a herpes-treating medicine for treatment of herpes.

\* \* \* \* \*